Figure 1:
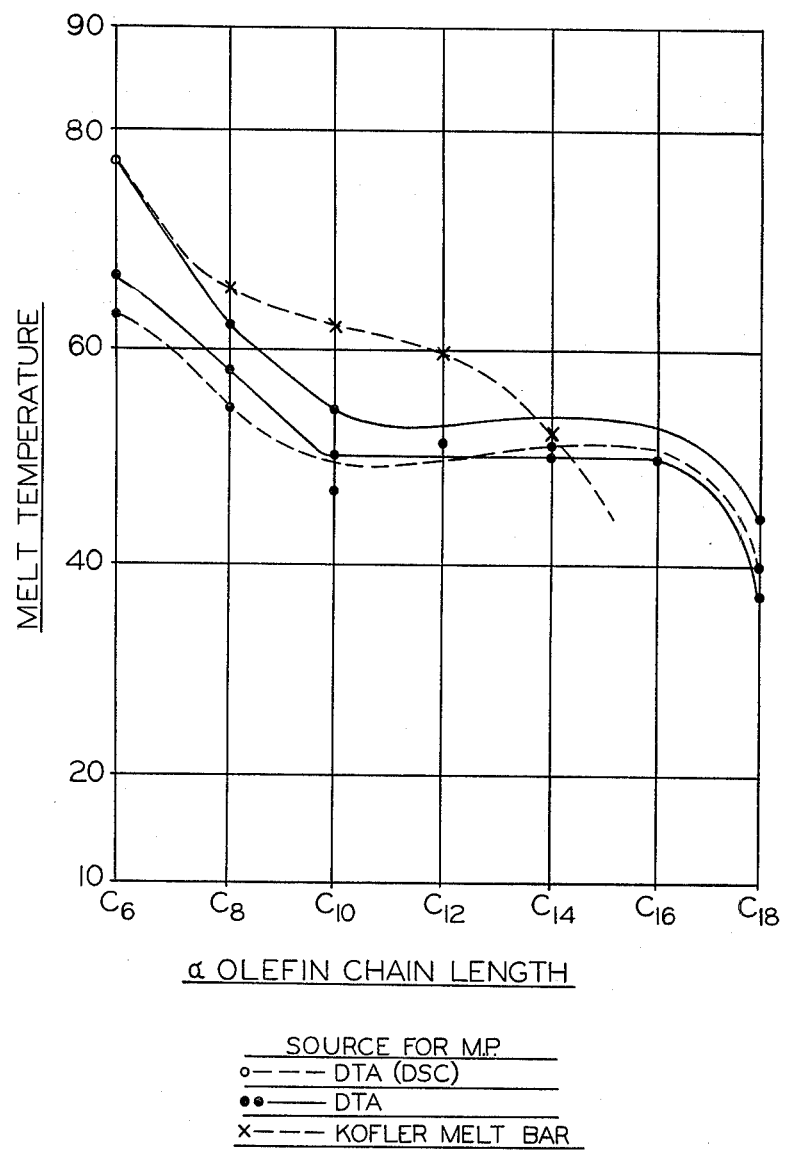

United States Patent [19]

Gray

[11] 4,423,930
[45] * Jan. 3, 1984

[54] POLYMERIC CONTACT LENS MATERIALS WITH HIGH OXYGEN PERMEABILITY

[75] Inventor: Don N. Gray, Sylvania, Ohio

[73] Assignee: Owens-Illinois, Inc., Toledo, Ohio

[*] Notice: The portion of the term of this patent subsequent to Dec. 23, 1992, has been disclaimed.

[21] Appl. No.: 246,238

[22] Filed: Mar. 23, 1981

Related U.S. Application Data

[60] Continuation-in-part of Ser. No. 81,062, Oct. 2, 1979, abandoned, which is a division of Ser. No. 684,683, May 10, 1976, Pat. No. 4,179,757, which is a continuation of Ser. No. 577,533, May 14, 1975, abandoned, which is a division of Ser. No. 328,972, Feb. 2, 1973, Pat. No. 3,928,294, which is a continuation-in-part of Ser. No. 279,877, Aug. 11, 1972, abandoned, which is a continuation-in-part of Ser. No. 228,240, Feb. 22, 1972, abandoned.

[51] Int. Cl.³ .............................................. G02C 7/04
[52] U.S. Cl. .................. 351/160 R; 528/386
[58] Field of Search ................ 528/386; 351/160 R

[56] References Cited

U.S. PATENT DOCUMENTS

| | | | |
|---|---|---|---|
| 2,190,836 | 2/1940 | Harmon | 528/386 |
| 3,728,185 | 4/1973 | Gray | 528/386 |
| 3,892,721 | 7/1975 | Gustafson | 528/320 |
| 3,928,294 | 12/1975 | Crawford | 528/386 |
| 4,179,757 | 12/1979 | Crawford | 528/386 |

Primary Examiner—C. A. Henderson
Attorney, Agent, or Firm—Wilson, Fraser, Barker & Clemens

[57] ABSTRACT

A series of alpha-olefin sulfur dioxide copolymers derived from the $C_4$ to $C_{18}$ alpha-olefins which may be readily processed to an optical article, such as a contact lens, having oxygen and carbon dioxide permeability which make them desirable in uses for contact lenses.

5 Claims, 12 Drawing Figures

SOFT CONTACT LENS

SURGICAL TUBING

POLYMERIC CONTACT LENS MATERIALS WITH HIGH OXYGEN PERMEABILITY

CROSS REFERENCES TO RELATED APPLICATIONS

This is a continuation-in-part of copending U.S. patent application Ser. No. 081,062, filed Oct. 2, 1979 now abandoned, which was a divisional application of Ser. No. 684,683, filed May 10, 1976 now U.S. Pat. No. 4,179,757, which was a continuation of Ser. No. 577,533, now abandoned, filed May 14, 1975 which was a division of Ser. No. 328,972, filed Feb. 2, 1973, now U.S. Pat. No. 3,928,,294, which was a continuation-in-part of Ser. No. 279,877 which was filed Aug. 11, 1972, now abandoned which was a continuation-in-part of Ser. No. 228,240, which was filed on Feb. 22, 1972, now abandoned.

BACKGROUND OF THE INVENTION

This invention relates to the preparation and use of polymeric materials which exhibit increased permeability, desirable optical properties and high biocompatibility. More particularly, this invention relates to the preparation of novel permselective membrane articles in a contact lens configuration consisting of an alpha-olefin/sulfur dioxide copolymer having high permeability to gases, especially to oxygen and carbon dioxide and having high biocompatibility.

Copolymers from simple olefins and sulfur dioxide have been known for some time. They were first reported by Matthews and Elder in British Pat. No. 11,635 in 1915, although the material prepared was not identified as being polymeric. Seyers and King, *J. Amer. Chem. Soc.*, 55, 3140, in 1933 were the first to accurately describe an olefin heteropolymer of sulfur dioxide. Characterization of these compounds as high molecular weight materials was accomplished independently by Marvel and Staudinger. Reference is made to *J. Amer. Chem. Soc.*, 56, 1915 (1934): *J. Amer. Chem. Soc.*, 57, 1691 (1935); and *Ber Bunsenges. Phys. Chem.*, 68,455 (1935). Both recognized that an AB-type copolymer was obtained regardless of monomer concentration, and they correctly deduced that the active polymerizing species was an olefin-sulfur dioxide complex. Marvel and Weil later showed the polysulfone structure to be a head-to-tail configuration as evidenced from the preparation of various compounds that were compared with the hydrolysis products of the polymers. See *J. Amer. Chem. Soc.*, 76, 61 (1954).

Marvel characterized a number of olefin-sulfur dioxide polymers using pyrolysis techniques. Naylor and Anderson, *J. Amer. Chem. Soc.*, 76, 3962 (1954), prepared copolymers of ethylene, propylene, 2-butene, and isobutylene with $SO_2$ at 65°–70° C. using radical catalysts. They found that the propylene-sulfur dioxide polymer started to degrade at about 180° C. with an activation energy of 32 kcal/mole determined from data obtained between 180° and 260° C. ($T_c$ for this polymer is 62.5° C.). Pyrolysis of the propylene-based polymer in nitrogen at 280°–290° C. yielded 95.5% volatile products, with 83.4% of the initial polymer weight being monomers. Water and some identified sulfur-containing compounds were also isolated.

This invention is related to the preparation and properties of poly(alpha-olefin sulfones) prepared from the series of $C_4$–$C_{18}$ alpha-olefins (both odd and even numbered) and sulfur dioxide and the use of these polymeric products as materials for the construction of contact lenses.

Polymeric materials having gaseous permeability are known in the prior art. The particular use of poly alkyl sulfones of very high permeability is described in U.S. Pat. Nos. 3,928,294 and 4,179,757. Prior to discovery of the extremely high permeability of this series of poly alkylsulfone polymers, most membrane devices were fabricated from material comprised of silicones or modified silicones. One such membrane device is the artificial lung. Another membrane device is the gas permeable plastic contact lens. The processing of silicones is sometimes difficult. In addition, pure silicone materials tend to have poor mechanical properties and must be filled with collidal silica and the like to yield a material capable of being processed. Such incorporation of fillers often compromises the optical properties of the silicone in addition to acting as a potential source of biological irritation.

Contact lenses formed of glass and, later, plastic material as described by Tuohy, U.S. Pat. No. 2,510,438, are well known. Such devices are widely used and function by remaining in intimate contact with the eyeball and, when properly fitted, the lens will accompany all movements of the eyeball. The advantage to visual correction of contact lenses as compared to spectacle lenses is well known. Spectacle lenses alter visual wave length radition before the rays reach the surface of the eye. Contact eye lenses, on the other hand, function as an integral part of the cornea altering the incident radiation at the surface of the eye.

A high quality contact lens must be optically transparent in the visible wave length region, biologically bland or inert, mechanically stable to maintain the optical correction and, lastly, should be permeable to gases. This latter requirement of permeability to oxygen and carbon dioxide is a requirement that is gaining in importance as the physiological requirements of the eye are further understood. In the history of the art of construction of contact lenses, the first materials to be used were glass and poly methylmethacrylate (PMMA). Glass presents a total barrier to the transmission of gases to the cornea, and PMMA has a very low permeability as shown in Table IV.

The cornea of the human eye will absorb about 5 cubic centimeters/square centimeter of oxygen an hour, and will release approximately four times this volume of carbon dioxide (R. M. Hill in "The Physiology of Soft Lens Systems" in *Soft Contact Lenses*, 1978). This phenomenon has been recognized for some time, but its effects on the fitting and wearing of contact lenses only became a concern with the wide usage of the PMMA lenses mentioned previously.

The cornea has an alternative method of compensating for oxygen deprivation by using more energy in the form of stored glucose. However, after about four hours, most of the glucose stored is depleted resulting in edema of the epithelial cell layer. This edema or swelling of the eye is extremely irritating. Many times the microcirculatory system of the eye dilates in an effort to adapt to oxygen deprivation by increasing the size of the capillaries causing the eye to become red. These effects occur with an awake open eye fitted with a barrier contact lens. When the eyelid is closed, there is even less opportunity for the passage of the essential gases.

To circumvent this problem, Ivani, U.S. Pat. No. 3,900,250 has proposed the use of cellulose acetate butyrate (CAB) as a material for rigid contact lens, since CAB has a higher oxygen permeability than PMMA.

Silicones have also been suggested as materials for the fabrication of soft contact lens, by Becker, U.S. Pat. No. 3,228,741. However, as stated earlier, silicones do not always lend themselves to facile fabrication techniques, and they usually must be reinforced with a particulate reinforcing agent to gain adequate strength for use, handling, etc.

SUMMARY OF THE INVENTION

It is an object of the present invention to provide a polymeric material having a gaseous permeability, biocompatibility and suitable mechanical properties which can readily be processed into a membrane.

A further object of this invention is to provide a polymeric material suitable for contact lenses which exhibits high biocompatibility and high permeability to oxygen and carbon dioxide.

More specifically, in accordance with this invention, there is provided a novel membrane article as actually having high permeability, excellent non-thrombogenic properties to blood, and improved mechanical properties and consisting of a poly(alpha-olefinsulfone) prepared from the series $C_6$ to $C_{18}$ alpha-olefins and sulfur dioxide, said poly(alpha-olefinsulfone) having the chemical structure:

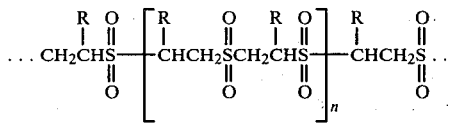

where R is a straight chained, branched, or cyclic alkyl hydrocarbon radical containing four (4) to sixteen (16) carbon atoms.

The polymer is typically prepared via the reaction:

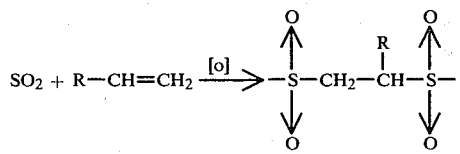

where [o] is any suitable catalyst such as a free radical source, light, peroxide, or azonitrile and where R is a straight chained, branched or cyclic alkyl hydrocarbon group of four (4) to sixteen (16) carbons.

It is contemplated reacting a mixture of alpha-olefins with the $SO_2$. Typically the $SO_2$ and the alpha-olefin(s) are reacted in a molar ration of 1:1.

The following represents certain experimental results and some of the best embodiments contemplated by the inventors in the practice of this invention.

MONOMER PURITY

Commercial alpha-olefins having a minimum monoolefin content of 98.5% (remainder being normal paraffins) were used in this study. Gas-chromatographic analysis showed less than 2% olefinic impurities consisting of other alpha-olefins.

POLYMERIZATION

Bulk polymerization was used to prepare the series based on the $C_4$-$C_{18}$ even and odd numbered alpha-olefins and sulfur dioxide. A clean, dry nitrogen-purged citrate bottle was cooled in an ice water bath, then liquified sulfur dioxide was added. The olefin containing 1% tert-butyl hydroperoxide, based on the olefin, was then added slowly to the citrate bottle. With an addition of a small amount of the olefin, approximately one-fourth of the total quantity, a rapid reaction occurred, resulting in a loss of some $SO_2$. After the remaining olefin-peroxide mixture was added, the bottle was capped with a lined, ventable cap and the contents were allowed to warm to room temperature. Following a predetermined reaction period, usually 20 hr. at room temperature, the bottle was vented and the contents were removed. The product was kept at reduced pressure to remove the residual monomers.

MOLECULAR WEIGHTS

Molecular weights ($M_n$) (membrane osmometer) were all above 100,000, and some were as high as 350,000.

DIFFERENTIAL THERMAL ANALYSIS

Polymer melt temperatures were obtained using the standard capillary (micro) cell of the duPont 900 instrument, the duPont 900 with the DSC cell module, and visually using a Kofler melt bar. These data are shown in FIG. 1. All melt data were obtained on polymers having molecular weight ($M_n$) in excess of 150,000. It was not possible to obtain accurate glass transistions since several other second-order transformations appeared to be occurring in the temperature region where one would expect the $T_g$ to occur.

THERMOGRAVIMETRIC ANALYSIS

Thermogravimetric analysis (TGA) was obtained on a duPont 900 unit in both air and nitrogen atmospheres. For screening purposes for a particular polymerization run, a heating rate of 20° C./min in air with a sample size of about 10–15 mg was used. Generally the polymer decomposed cleanly. Pyrolysis started at 175° C. and was essentially complete when the temperature reached 275° C. One $C_{14}$ polymer sample ($M_n$ 136,000) was used to obtain kinetic data (pyrolysis) using the method of Wall and Flynn, Polymers Letters, 4, 323 (1966). TGA data were obtained at heating rates of 5°, 10°, 15° and 20° C./min in air. The average activation energy for the pyrolytic decomposition was found to be 46–47 kcal/mole.

MASS-SPECTROMETRIC THERMAL ANALYSIS AND PYROLYSIS GAS-CHROMATOGRAPHIC ANALYSIS

Mass-spectrometric thermal analysis was accomplished using the solid sample wand of the Varian M-66 mass spectrometer. The sample used was the $C_{14}$ polymer used for the kinetic TGA runs. A wand temperature of 250° C. yielded mass spectra differing only from the fragmentation pattern of the pure $C_{14}$-alpha-olefin by peaks at 64 and 48 mass units corresponding to the $SO_2$ and SO ion species.

For higher temperature pyrolysis studies, pyrolysis gas chromatrography was utilized. A Perkin-Elmer pyrolyzer was connected to a gas chromatograph equipped with a hydrogen flame detector and a 20% carbowax/firebrik column. Separate samples of the $C_{14}$ copolymer were heated rapidly to 400°, 600°, and 800° C. in the pyrolysis chamber. At 400° C., only the $C_{14}$-alpha-olefin was detected. At 600° C. about equal amounts of the olefin and lighter pyrolysis products were found, while at 800° C., only complete pyrolysis products consisting of methane, ethylene, ethane, propylene, and propane were found.

DENSITY

Figure 2:
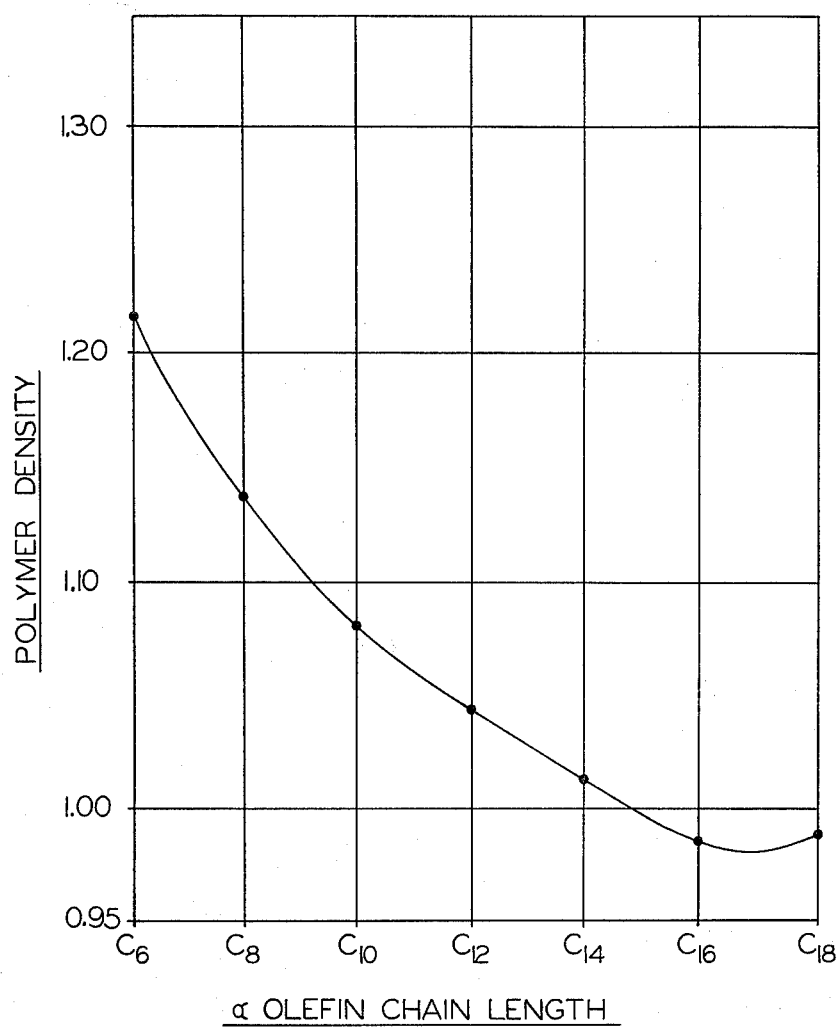

Density as a function of chain length was determined on the polymer series using a density gradient column. These data are shown in FIG. 2.

PERMEABILITY

The gaseous permeability to oxygen and carbon dioxide of this series of polymers is quite high, with only the silicones and modified silicones showing high permeability. The relationship between alpha-olefin chain length and gaseous oxygen permeability for selected members of the $C_4$–$C_{18}$ series is plotted in FIG. 3. Permeability was determined by a modified Linde volumetric cell on films from polymers having molecular weight in excess of 150,000 ($M_n$)

TENSILE MODULUS AND ELONGATION

Samples of polymers from the same polymerization run as those submitted for permeability studies were used to determine the mechanical properties (tensile modulus, percent elongation, and ultimate elongation). These are presented in FIGS. 4 and 5.

Data were obtained in accordance with ASTM Method No. 1708 with a cross-head speed of 0.5 in./min., the gauge length 0.90 in., a chart speed of 20 in./min., 74° F., and a relative humidity of 53%.

RESULTS AND DISCUSSION

It has been recognized that the olefin-$SO_2$ copolymers are not thermally stable and that thermal degradation occurs via an unzipping mechanism to yield mostly monomers. Mass-spectrometric thermal analysis indicates that the original comonomers are the only products of vacuum-pyrolytic degradation, and no other sulfur-containing products were found such as described by Naylor and Anderson; *J. Amer. Chem. Soc.*, 76, 3962 (1954).

At higher temperatures under essentially flash pyrolysis conditions, the decomposition mechanism appears to be a chain-unzipping one to form the alpha-olefin and sulfur dioxide, followed by the pyrolysis of the alpha-olefin. An activation energy for degradation of approximately 46 kcal/mole is in line with a similar activation energy for pyrolysis of other chain-unzipping polymers such as polystyrene, variously reported from 55 to 70 kcal/mole, and poly(methyl methacrylate), a good average being 40 kcal/mole. Initiation of degradation is in the 175° C. range, and pyrolysis is generally complete at 225° C. with a heating rate of 20° C./min. It is noted that this value given for the activation energy is for the pyrolysis of the molten polymer, since the polymer melt temperatures for all of the polymers were well below their 175° C. decomposition points. There is no real difference in the pyrolysis characteristics of the polymers as a function of chain length of the alpha-olefin comonomer. This is not unexpected since the rate-determining step must involve an end group initiation or a chain scission of a carbon-sulfur linkage. The alpha-olefin tail could be expected to play no great part in guiding the course of the pyrolytic reaction.

VARIATION OF PROPERTIES OF FUNCTION OF CHAIN LENGTH

In the series studied, the polysulfones prepared from the commercial olefins range from a hard, tough material prepared from the $C_4$-alpha-olefin to an elastomer obtained from the $C_{16}$-olefin and the permeabilities of oxygen and carbon dioxide reach a maximum at the $C_{16}$-based polymer. Also the tensile and elongation curves show a break at the $C_{16}$-polymer. In addition, the minimum density is obtained with the $C_{16}$-based polymer as shown in FIG. 2. Our explanation for this behavior is that a plasticizing effect with the longer alpha-olefin chain is occurring since it can be shown that a $C_{16}$ alpha-olefin can flexibilize a $C_6$-alpha-olefin-sulfone polymer. The plasticizing effect should become more efficient as the chain length of the alpha-olefin increases. However, we believe another effect occurs at $C_{18}$, specifically, side chain crystallization. In this case the olefin side chain crystallizes independently of the backbone of the polymer, thus lowering its mobility and its plasticizing action on the main chain of the polymer. Side chain crystallization has been noted in several other monologous series of polymers. Overberger and co-workers, *J. Amer. Chem. Soc.*, 75, 3326 (1953), studied a series of poly(para-alkyl styrenes) with the normal aliphatic groups ($C_2$–$C_{10}$) substituted in the para position. They found a maximum in the glass transition temperature occurring with the $C_{10}$ side chain. If one adds the length of a four-carbon unit for the approximate size of the para-phenylene moiety, then the total chain length would be similar to a $C_{14}$ carbon chain rather than a $C_{10}$ chain:

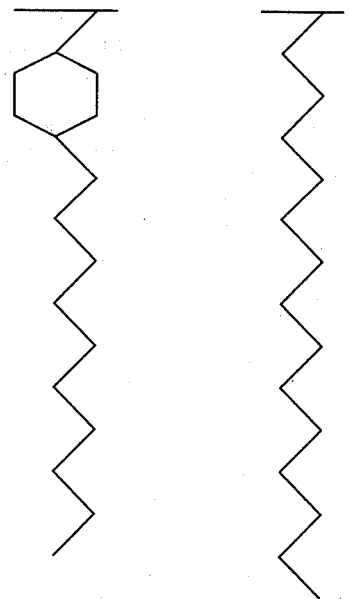

No direct evidence (x-ray data, etc.) was obtained for crystallinity in the polymers prepared. This does not rule out the proposed explanation for the variation in properties as function of chain legth, since small-size crystallites cannot always be recognized in a polymeric matrix by x-ray analysis techniques. Purity of the monomer feed stock was ruled out as a factor for this variation since a similar trend was found for polymers prepared from highly purified monomers. The permeation data obtained from the ter polymer systems (Table I) also support this theory of of competitive plasticization versus side chain crystallization as a causative factor for the maximum obtained for the physical properties.

TABLE I

PERMEABILITY OF TERPOLYMERS

| Olefin[a] | $O_2$ transmission cc-mil/in²-yr-atm | $CO_2$ transmission, cc-mil/in²-yr-atm |
|---|---|---|
| 90 Hexene-10 hexadecene | 1,860 | 6,870 |
| 90 Hexene-10 hexadecene (plasticized)[b] | 4,340 | |
| 50 Hexene-50 hexadecene | 9,960 | 49,630 |
| 16.7 Hexene-83.3 hexadecene | 33,070 | 110,250 |
| 3.3 Hexene-96.7 hexadecene | 37,530 | 142,300 |
| 16.7 Hexadecene-83.3 octadecene | 34,730 | 154,700 |
| 50 Hexadecene-50 octadecene | 46,700 | 191,900 |

[a]Figures before olefin indicate concentration in wt-%.
[b]Hexadecene, 10 wt-%, used as a plasticizer for the hexene-sulfur dioxide copolymer.

Many membrane devices have been constructed of silicone rubber materials largely because of their high oxygen and carbon dioxide permeabilities and their reasonable non-thrombogenic properties. However, the poor mechanical properties of pure polysilicone materials require the use of high concentrations of silica filler which compromise their ultimate performance as a blood compatible biomaterial. This invention, as described herein, utilizes a material not to our knowledge previously evaluated for blood oxygenation purposes and which shows better physical properties in the pure state than silicone rubber, and also comparable gas permeability and nonthrombogenic properties relative to silicone rubber.

For example, to illustrate the high biocompatibility towards blood, the classical Lee-White clotting time method was used. (R. I. Lee and P. D. White. "A Clinical Study of the Coagulation Time of Blood", Am. J. Med. Sci. 145, 495 (1913).

The following average whole blood clotting times (WBCT) were obtained for borosilicate glass and the $C_{16}$ olefin-based polysulfone:

TABLE II

| Surface | Lee-White Clotting Time (min) |
|---|---|
| Glass, borosilicate (Pyrex) | 8.0 |
| Polysulfone coated pyrex glass | 27.0 |

A typical literature WBCT value for silicone rubber is 27 minutes (Boretos, J. W., Pierce, W. S. "Segmented Polyurethane: A Polyether Polymer. An Initial Evaluation for Biomedical Applications." J. Biomed. Mater. Res. Vol. 2, p. 12, (1968).

The high biocompatibility of the polysulfones of this invention, as illustrated by the foregoing Lee-White test, indicates that this material will have utility for the fabrication of prosthetic devices in contact with body fluids, for example, heart valves, surgical implants, artificial arteries and veins, soft contact lenses, and drug delivery systems.

In addition, the high biocompatibility coupled with high permeability suggests their utility for surgical tape and wound dressings.

The inate flexibility and ease of forming, both by solvent casting and thermoplastic extrusion, coupled with the high biocompatibility suggests their use for surgical tubing as for example in blood transfusion, intraveneous feedings, etc.

To indicate the utility of permeable membranes as blood oxygenators, a man at rest consumes approximately 18 liters per hour of oxygen. Therefore, about two square yards of the $C_{16}$ based polysulfone polymer fabricated into a well designed perfusion device would be adequate for life support.

The high permeability of the polysulfone polymers coupled with their potential low cost makes them commercially interesting. These polymers have excellent flexibility, fair transparency and solvent castability. They can be extruded and heat-sealed.

Permselective membranes have also been used for: instrumentation for gas analysis; separation, purification and enrichment of gases; preventing passage of microorganisms in the pharmaceutical and fermentation industries. Also for surgical dressings and breathing systems in general.

Note that from plot of oxygen transmission versus thickness (FIG. 13), it can be seen that all members of the series PAS-6 to PAS-16, that is the alpha-olefin series of copolymers prepared from alpha-olefin from hexene to hexadecene have oxygen transmission values in excess of CAB for all useful lens thicknesses.

For purposes of comparison, the permeability coefficients to oxygen of the poly alpha-olefin sulfones prepared from 1-hexadecene (PAS-16), 1-octene (PAS-8), 1-hexene (PAS-6) and 1-butene (PAS-4), cellulose acetate butyrate (CAB) and polymethylmethacrylate (PMMA) are shown in Table III.

TABLE III

PERMEABILITY COEFFICIENTS

| POLYMER | PERMEABILITY COEFFICIENT (Pg)* |
|---|---|
| PAS-16 | 7 |
| PAS-8 | 2 |
| PAS-4 | 1.5 |
| Cellulose Acetate Butyrate (CAB) | 0.6 |
| Polymethylmethacrytate (PMMA) | 0.01 |

Figure 3:
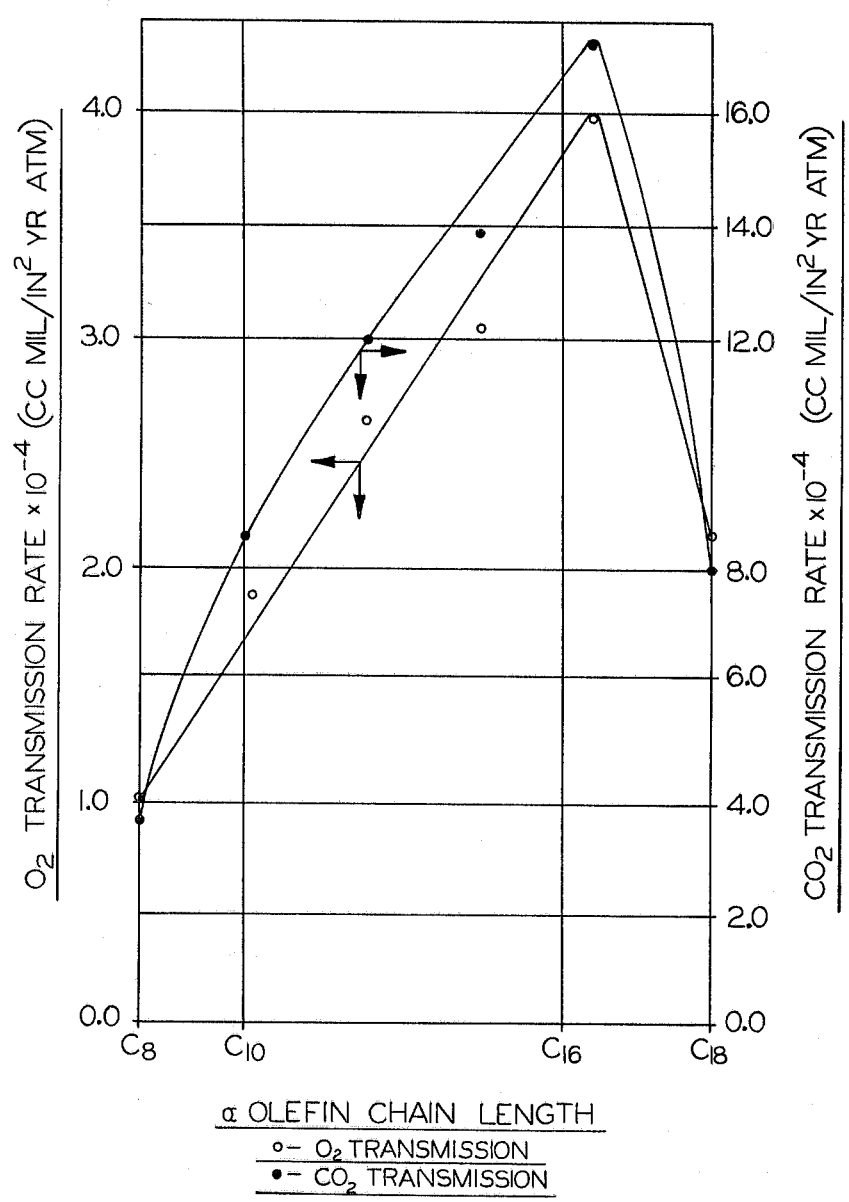
Figure 4:
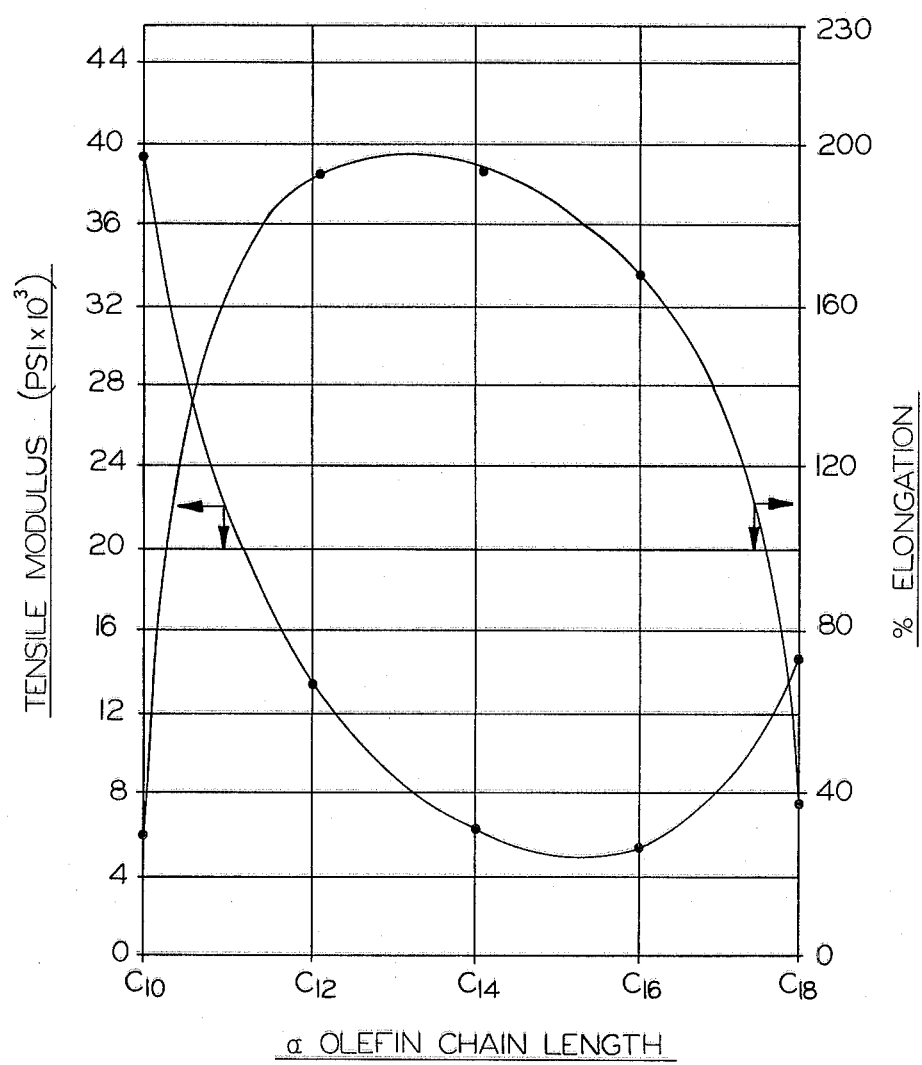
Figure 5:
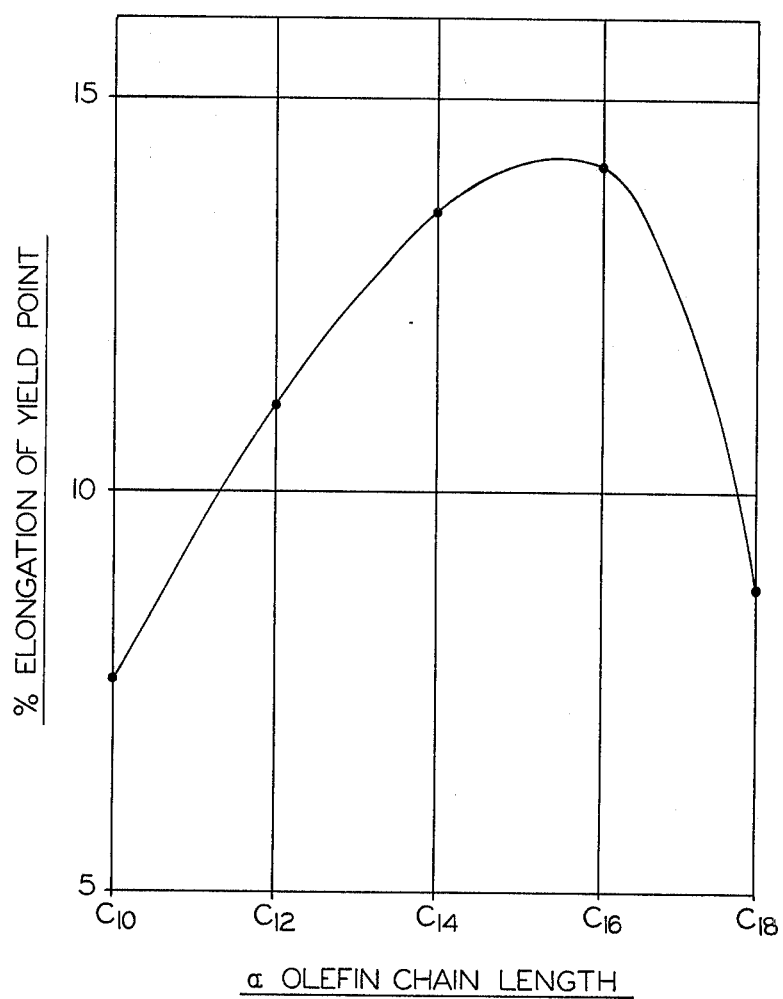

*Permeability Coefficient (Pg) (Gas-to-gas) = $\dfrac{cm^3 \, O_2 \cdot mm}{cm^2 \cdot sec \cdot \Delta cmHg} \cdot 10^{-10}$ The physical properties of the copolymers are illustrated in FIGS. 1 through 5, FIG. 1 showing a plot of the alpha-olefin chain length (containing from $C_6$ to $C_{18}$ carbon atoms) against the melt temperature. FIG. 2 plots the alpha-olefin chain lengths from $C_6$ to $C_{18}$ carbon atoms against polymer density. FIG. 3 indicates the relationship between the olefin chain length and the $O_2$ transmission. FIG. 4 plots the alpha-olefin chain length against tensile modulus and percent elongation. FIG. 5 plots the alpha-olefin chain length against the percent elongation at yield point.

Figure 6:

The use of the alpha-olefin/$SO_2$ copolymer is illustrated in FIG. 6 which shows a soft contact lens article 5 made from the readily processable copolymer of the alpha-olefin and $SO_2$.

Figure 7:
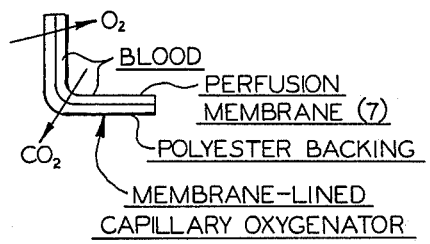

The membrane 7 is supported by a polyester backing and is used, for instance, in a membrane-lined, capillary oxygenator. As seen in FIG. 7, the membrane 7, made of the alpha-olefin/$SO_2$ copolymer, is in contact with blood. The arrows show $O_2$ entering the blood supply while $CO_2$ leaves the blood through the membrane and the porous polyester backing which, in turn, is supported on porous substrate such as shown, for example, in the membrane-lined capillary oxygenator shown on page 139 of Transactions, American Society for Artificial Internal Organs, 1969.

The copolymers of alpha-olefin and SO$_2$ can be used in many of the biocompatible articles used in contact with body fluids such as artificial arteries, artificial veins, heart valves, surgical implants, blood storage bags and surgical tubing, illustrated in the above article, for example, on pages 170, 173, 179, 201, 212, 207, 246, 251, 256, 287 and 352.

Figure 8:
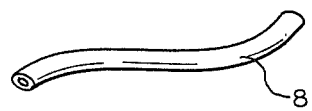

FIG. 8 shows a biocompatible article 8 for contact with human body fluids made of a copolymer of an alpha-olefin and sulfur dioxide, the article being surgical tubing.

Figure 9:
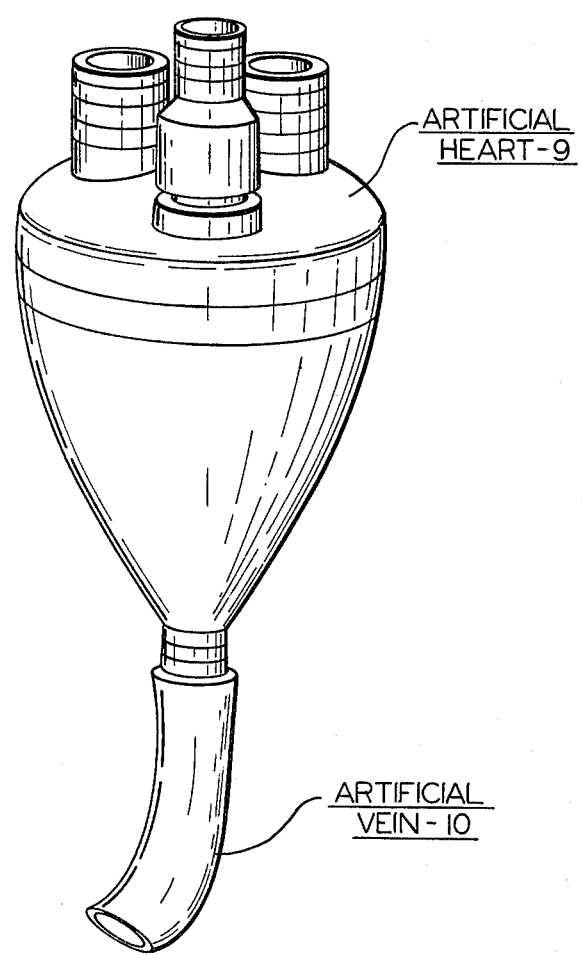
Figure 10:
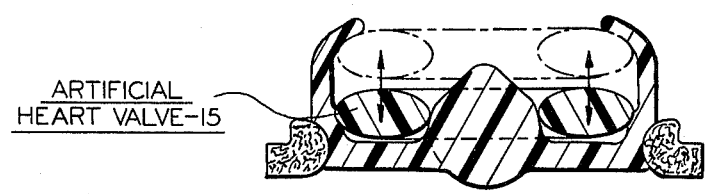
Figure 11:
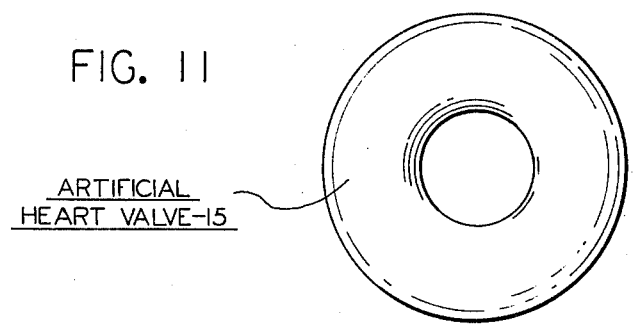

FIG. 9 illustrates a biocompatible article for contact with human body fluids, the article being an artificial heart 9, and an artificial vein 10 connected to the heart. As indicated previously, the biocompatible copolymer of alpha-olefin and sulfur dioxide can be used as an artificial heart valve, which is shown as valve 15 in FIG. 10. The valve 15 is toroidal in shape, and a perspective view of the toroidal valve 15 is shown in FIG. 11.

Figure 12:
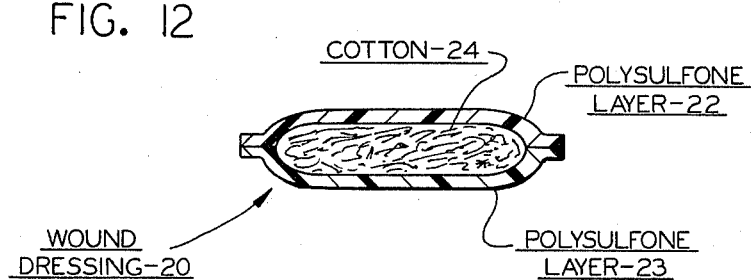

FIG. 12 illustrates another biocompatible article for use in contact with body fluids, the article being a wound dressing 20. The wound dressing 20 comprises a pair of porous polysulfone (copolymer of an alpha-olefin and SO$_2$) layers 22 and 23 with cotton between the two layers. As also shown in FIG. 12, the ends of the polysulfone layers are sealed to provide an excellent dressing.

As previously indicated, outstanding results have been obtained by the use of the alpha-olefin/SO$_2$ copolymers described herein, including the new use of the biocompatible polymer comprising the steps of (1) making a biocompatible article for contact with human body fluids, the article being made of a copolymer of (a) an alpha-olefin having 4 to 18 carbon atoms and (b) sulfur dioxide, and (2) contacting human body fluids with the article of step 1 to provide a nonthrombogenic article having good oxygen and carbon dioxide permeabilities.

What is claimed is:

1. As an article of manufacture, a soft contact lens article made of a copolymer having the requisite degree of optical clarity and permeability to CO$_2$, and a permeability to oxygen at least as great as that of cellulose acetate butyrate, measured under the same conditions, and that is a biocompatible reaction product of
   (1) an alpha-olefin having 6 to 18 carbon atoms and
   (2) sulfur dioxide.
2. An article as defined in claim 1 in which the alpha-olefin has 16 carbon atoms.
3. An article as defined in claim 1 in which said alpha-olefin is a mixture of two-alpha-olefins such that the article of manufacture is a random terpolymer of two alpha-olefins and sulfur dioxide.
4. An article of manufacture as defined in claim 1 in which the alpha-olefin has 6 carbon atoms.
5. An article of manufacture as defined in claim 1 in which the alpha-olefin has 8 carbon atoms.

* * * * *